US011892580B2

(12) United States Patent
Little (10) Patent No.: US 11,892,580 B2
(45) Date of Patent: Feb. 6, 2024

(54) DECOMPACTION OF SUBSURFACE REGION USING DECOMPACTION VELOCITY

(71) Applicant: Chevron U.S.A. Inc., San Ramon, CA (US)

(72) Inventor: Robert Lewis Little, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 136 days.

(21) Appl. No.: 17/148,111

(22) Filed: Jan. 13, 2021

(65) Prior Publication Data

US 2022/0221605 A1 Jul. 14, 2022

(51) Int. Cl.
*G01V 1/30* (2006.01)
*G01N 33/24* (2006.01)

(52) U.S. Cl.
CPC .......... *G01V 1/305* (2013.01); *G01N 33/246* (2013.01); *G01V 1/306* (2013.01)

(58) Field of Classification Search
CPC ....... G01V 1/305; G01V 1/306; G01N 33/246
See application file for complete search history.

(56) References Cited

U.S. PATENT DOCUMENTS

| | | | | |
|---|---|---|---|---|
| 8,739,867 B2 * | 6/2014 | Panter | ................ | B09C 1/02 166/371 |
| 10,520,644 B1 * | 12/2019 | Mallet | ................ | G06T 19/20 |
| 10,705,254 B1 * | 7/2020 | Mallet | ................ | G06T 17/05 |
| 11,156,744 B2 * | 10/2021 | Mallet | ................ | G06T 19/20 |
| 2019/0383965 A1 * | 12/2019 | Salman | ................ | G01V 11/00 |
| 2020/0225382 A1 * | 7/2020 | Mallet | ................ | G06T 17/05 |
| 2020/0225383 A1 * | 7/2020 | Mallet | ................ | G06T 19/00 |
| 2021/0389498 A1 * | 12/2021 | Michael | ................ | G01V 99/005 |

FOREIGN PATENT DOCUMENTS

CN 110905480 A * 3/2020

OTHER PUBLICATIONS

M. Vanaki and et al, "Direct Application of Geophysical/Seismic Methods for N/G Calculation", Abu Dhabi International Petroleum Exhibition and Conference, Abu Dhabi, United Arab Emirates, Oct. 10-13, 2004 (Year: 2014).*

(Continued)

*Primary Examiner* — Douglas Kay
(74) *Attorney, Agent, or Firm* — Esplin & Associates, PC (57) ABSTRACT

The thickness of subsurface layers if they had remained as they were prior to compaction may be estimated by restoring the volume of void space lost during compaction. Decompacted depths below seafloor, the depths the layers would be if compaction had not occurred, may be determined for the layers. A surrogate decompaction velocity may then be determined by dividing the decompacted depths by the travel times of acoustic waves that reflect off layers within the subsurface region. The decompaction velocity may be used in post-processing of acoustic data to produce a decompacted digital representation of the subsurface region. The decompacted digital representation may be used to directly interpret the thickness of layers prior to compaction, sedimentation rates over time, fault offsets, and other phenomena distorted by compaction.

16 Claims, 7 Drawing Sheets

(56) References Cited

OTHER PUBLICATIONS

M. Al-Chalabi and Peter L. Rosenkranz, "Velocity-depth and time-depth relationships for a decompacted uplifted unit", Geophysical Prospecting, vol. 50, Issue 6, Jun. 2002, p. 661-664 (Year: 2020).*
Z. Lv and et al., "The Application of 3D tectonic restoration and dynamic strain in Strike-slip tectonic belt, A case study from Bohai Bay Basin, NE China", SEG International Exposition and 89th Annual Meeting, 2019 (Year: 2019).*

* cited by examiner

DECOMPACTION OF SUBSURFACE REGION USING DECOMPACTION VELOCITY

FIELD

The present disclosure relates generally to the field of decompacting subsurface data using decompaction velocity of acoustic waves within a subsurface region.

BACKGROUND

Compaction of sediments in a subsurface region may increase as increasing amount of soil is deposited on top of each other. Such compaction of soil, if unaccounted for when interpreting acoustic data, may result in underestimation of past events within the subsurface region, such as underestimation of historic sedimentation rates, fault offsets, and/or mass gravity flow effects. Such underestimation may cause errors in quantification of geohazard risk.

SUMMARY

This disclosure relates to decompacting subsurface data. Acoustic information, void information, and/or other information for a subsurface region may be obtained. The acoustic information for the subsurface region may characterize travel times of acoustic waves that reflected off layers within the subsurface region. The void information for the subsurface region may characterize void amount of the layers within the subsurface region.

Decompacted void amount of the layers within the subsurface region may be determined. The decompacted void amount may represent amount of void within the layers before compaction of the layers. Decompaction velocity for the layers within the subsurface region may be determined based on the decompacted void amount of the layers within the subsurface region, and/or other information. Decompacted thickness of the layers within the subsurface region may be determined based on the decompaction velocity for the layers within the subsurface region, the travel times of the acoustic waves that reflected off the layers within the subsurface region, and/or other information.

A system that decompacts subsurface data may include one or more electronic storage, one or more processors and/or other components. The electronic storage may store acoustic information, information relating to travel time of acoustic wave, information relating to a subsurface region, information relating to layers within a subsurface region, void information, information relating to void amount of layers within a subsurface region, information relating to decompacted void amount, information relating to decompaction velocity, information relating to decompacted thickness of layers within a subsurface region, and/or other information.

The processor(s) may be configured by machine-readable instructions. Executing the machine-readable instructions may cause the processor(s) to facilitate decompacting subsurface data. The machine-readable instructions may include one or more computer program components. The computer program components may include one or more of an acoustic information component, a void information component, a decompacted void amount component, a decompaction velocity component, a decompacted thickness component, and/or other computer program components.

The acoustic information component may be configured to obtain acoustic information for a subsurface region and/or other information. The acoustic information may characterize travel times of acoustic waves that reflected off layers within the subsurface region.

The void information component may be configured to obtain void information for the subsurface region and/or other information. The void information may characterize void amount of the layers within the subsurface region.

In some implementations, the void amount may include a ratio of fluid to solids within a subsurface volume. In some implementations, the ratio of fluid to solids within the subsurface volume may be determined based on measurement of moisture content within the subsurface volume and/or other information.

The decompacted void amount component may be configured to determine decompacted void amount of the layers within the subsurface region. The decompacted void amount may represent amount of void within the layers before compaction of the layers. In some implementations, the ratio of fluid to solids within the subsurface volume may be increased in the decompacted void amount of the layers within the subsurface region.

The decompaction velocity component may be configured to determine decompaction velocity for the layers within the subsurface region. The decompaction velocity for the layers within the subsurface region may be determined based on the decompacted void amount of the layers within the subsurface region, and/or other information.

In some implementations, determining the decompaction velocity for the layers within the subsurface region based on the decompacted void amount of the layers within the subsurface region may include: determining expanded thickness of the layers based on the decompacted void amount of the layers; and determining the decompaction velocity for the layers based on the expanded thickness of the layers and the travel times of acoustic waves that reflected off the layers within the subsurface region.

The decompacted thickness component may be configured to determine decompacted thickness of the layers within the subsurface region. The decompacted thickness of the layers within the subsurface region may be determined based on the decompaction velocity for the layers within the subsurface region, the travel times of the acoustic waves that reflected off the layers within the subsurface region, and/or other information.

In some implementations, determining the decompacted thickness of the layers within the subsurface region based on the decompaction velocity for the layers within the subsurface region and the travel times of the acoustic waves that reflected off the layers within the subsurface region may include generating a decompacted digital representation of the subsurface region. The decompacted digital representation of the subsurface region may be generated by applying the decompaction velocity for the layers within the subsurface region to the travel times of the acoustic waves that reflected off the layers within the subsurface region.

In some implementations, analysis of past events within the subsurface region may be performed based on the decompacted digital representation of the subsurface region and/or other information. In some implementations, the past events within the subsurface region may include fault activity within the subsurface region. In some implementations, the past events within the subsurface region may include erosion and deposition within the subsurface region. In some implementations, usage of the decompacted digital representation of the subsurface region for the analysis of the past events within the subsurface region may reduce underestimation of the past events within the subsurface region.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a," "an," and "the" include plural referents unless the context clearly dictates otherwise.

DETAILED DESCRIPTION

The present disclosure relates to decompacting subsurface data. The thickness of subsurface layers if they had remained as they were prior to compaction may be estimated by restoring the volume of void space lost during compaction. Decompacted depths below seafloor, the depths the layers would be if compaction had not occurred, may be determined for the layers. A surrogate decompaction velocity may then be determined by dividing the decompacted depths by the travel times of acoustic waves that reflect off layers within the subsurface region. The decompaction velocity may be used in post-processing of acoustic data to produce a decompacted digital representation of the subsurface region. The decompacted digital representation may be used to directly interpret the thickness of layers prior to compaction, sedimentation rates over time, fault offsets, and other phenomena distorted by compaction.

Figure 1:
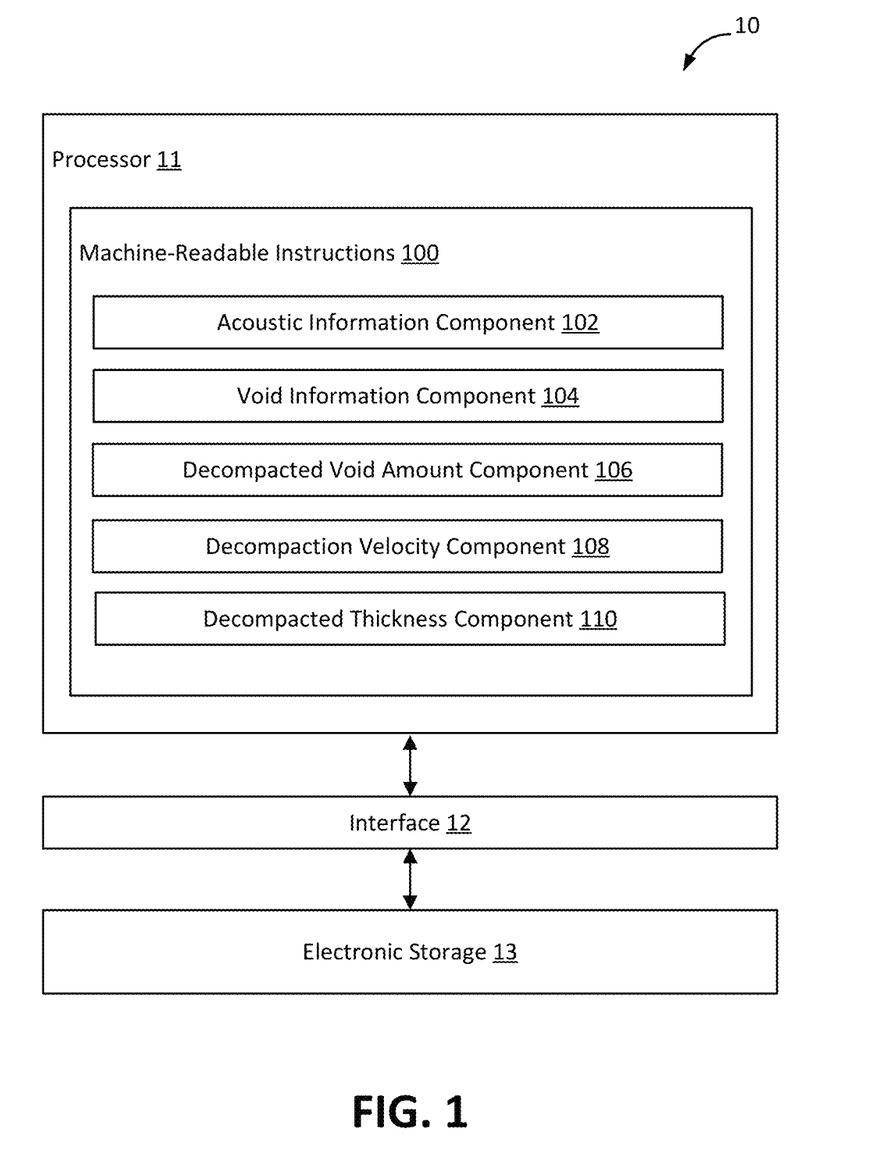
FIG. 1 illustrates an example system that decompacts subsurface data.

The methods and systems of the present disclosure may be implemented by and/or in a computing system, such as a system 10 shown in FIG. 1. The system 10 may include one or more of a processor 11, an interface 12 (e.g., bus, wireless interface), an electronic storage 13, and/or other components. Acoustic information, void information, and/or other information for a subsurface region may be obtained by the processor 11. The acoustic information for the subsurface region may characterize travel times of acoustic waves that reflected off layers within the subsurface region. The void information for the subsurface region may characterize void amount of the layers within the subsurface region.

Decompacted void amount of the layers within the subsurface region may be determined by the processor 11. The decompacted void amount may represent amount of void within the layers before compaction of the layers. Decompaction velocity for the layers within the subsurface region may be determined by the processor 11 based on the decompacted void amount of the layers within the subsurface region, and/or other information. Decompacted thickness of the layers within the subsurface region may be determined by the processor 11 based on the decompaction velocity for the layers within the subsurface region, the travel times of the acoustic waves that reflected off the layers within the subsurface region, and/or other information.

The electronic storage 13 may be configured to include electronic storage medium that electronically stores information. The electronic storage 13 may store software algorithms, information determined by the processor 11, information received remotely, and/or other information that enables the system 10 to function properly. For example, the electronic storage 13 may store acoustic information, information relating to travel time of acoustic wave, information relating to a subsurface region, information relating to layers within a subsurface region, void information, information relating to void amount of layers within a subsurface region, information relating to decompacted void amount, information relating to decompaction velocity, information relating to decompacted thickness of layers within a subsurface region, and/or other information.

The processor 11 may be configured to provide information processing capabilities in the system 10. As such, the processor 11 may comprise one or more of a digital processor, an analog processor, a digital circuit designed to process information, a central processing unit, a graphics processing unit, a microcontroller, an analog circuit designed to process information, a state machine, and/or other mechanisms for electronically processing information. The processor 11 may be configured to execute one or more machine-readable instructions 100 to facilitate decompacting subsurface data. The machine-readable instructions 100 may include one or more computer program components. The machine-readable instructions 100 may include one or more of an acoustic information component 102, a void information component 104, a decompacted void amount component 106, a decompaction velocity component 108, a decompacted thickness component 110, and/or other computer program components.

The acoustic information component 102 may be configured to obtain acoustic information for a subsurface region and/or other information. Obtaining acoustic information may include one or more of accessing, acquiring, analyzing, creating, determining, examining, generating, identifying, loading, locating, opening, receiving, retrieving, reviewing, selecting, storing, utilizing, and/or otherwise obtaining the acoustic information. The acoustic information component 102 may obtain acoustic information from one or more locations. For example, the acoustic information component 102 may obtain acoustic information from a storage location, such as the electronic storage 13, electronic storage of a device accessible via a network, and/or other locations. The acoustic information component 102 may obtain acoustic information from one or more hardware components (e.g., a computing device, a component of a computing device) and/or one or more software components (e.g., software running on a computing device). Acoustic information may be stored within a single file or multiple files.

The acoustic information may include information collected from a subsurface region. A subsurface region may refer to a part of earth located beneath the surface, located underground, and/or located under water. A subsurface region may refer to a part of earth that is not exposed at the surface of the ground. A layer may refer to a grouping of similar/same materials in the subsurface region. A subsurface region may include multiple layers stacked on top of each other.

The acoustic information may include information about the subsurface region obtained through one or more measurements. The acoustic information may include information about movement of acoustic waves within the subsurface region. The subsurface region may include layers, and the acoustic information may include information about reflection of the acoustic waves off the layers. For instance, the acoustic information may include seismic data (e.g., reflection seismic data) for the subsurface region. For example, the acoustic information may include seismic reflection measurements within the subsurface region and/or information calculated from seismic reflection measurements within the subsurface region, such as how long it took the acoustic waves to travel down to and reflect off layers within the subsurface region, and/or the velocity of the acoustic waves within the subsurface region. Acoustic wave reflection off layers may include reflection of acoustic wave off reflector between layers. A reflector may refer to an interface between layers of contrasting acoustic, optical and/or electromagnetic properties. A reflector may represent a change in subsurface properties, lithology, a fault, or an unconformity. The velocity of the acoustic waves within the subsurface region may include P wave velocity and/or other velocity of the acoustic waves. The velocity of the acoustic waves within the subsurface region may depend on the type and/or density of material between/within the layers within the subsurface region. In some implementations, the acoustic information may include sub-seafloor geophysical data, such as sub-bottom profiler data.

The acoustic information may characterize travel times of acoustic waves that reflected off layers within the subsurface region and/or other information relating to the acoustic waves within the subsurface region. Travel times of acoustic waves that reflected off layers within the subsurface region may include the length of time it took for the acoustic waves to penetrate into the subsurface region, bounce off the layers, and return for recording/detection. Travel times of acoustic waves that reflected off layers within the subsurface region may include the length of time it took for the acoustic waves to travel through one or more layers. The travel times of the acoustic waves and the velocity of the acoustic waves may be used to determine the thickness/depth of layers within the subsurface region.

The acoustic information may characterize the travel times of the acoustic waves within the subsurface region by including information that defines, describes, delineates, identifies, is associated with, quantifies, reflects, sets forth, and/or otherwise characterizes one or more of content, quality, attribute, feature, and/or other aspects of the travel times of the acoustic waves within the subsurface region. For example, the acoustic information may characterize the travel times of the acoustic waves by including information that specifies the travel times of the acoustic waves and/or information that is used to determine the travel times of the acoustic waves. Other types of acoustic information are contemplated.

The acoustic information may be processed to generate digital representation of the subsurface region, such as digital representation of subsurface features and/or stratigraphy. For instance, for subsurface region under the sea, normally deposited marine sediment may appear as a sequence of reflectors conformable to the seafloor surface. The depth of the reflectors may be referenced in terms of travel times of the acoustic waves from the source (e.g., acoustic wave generator/transmitter) to the receiver (e.g., acoustic wave detector/receiver). The time measurements of the acoustic wave travel times may be converted to physical distance below the seafloor by applying a profile of velocity of the acoustic wave through the sediment. This conversion may provide a distance measurement between layers and/or other features within the subsurface region. The distance measurement provided through such conversion may only provide the distance between the layers at the time of measurement, such as thickness/depth of layers that have been compacted by the time of measurement.

Figure 3A:
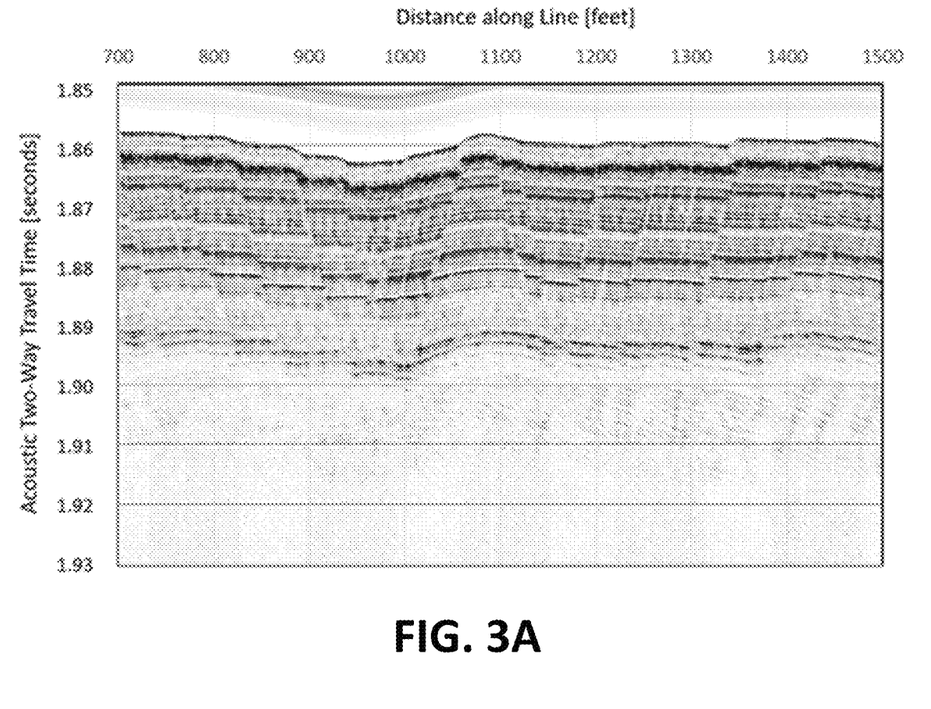
FIG. 3A illustrates an example digital representation of a subsurface region.

FIG. 3A illustrates an example digital representation of a subsurface region. The digital representation provides visual representation of layers and/or other subsurface features within the subsurface region. The digital representation may provide visual representation of locations of layers and/or other subsurface features as a function of acoustic wave travel time (e.g., acoustic two-way travel time for the acoustic waves to travel down to a reflector between layers, reflect off the reflector, and travel up to be detected).

Figure 3B:
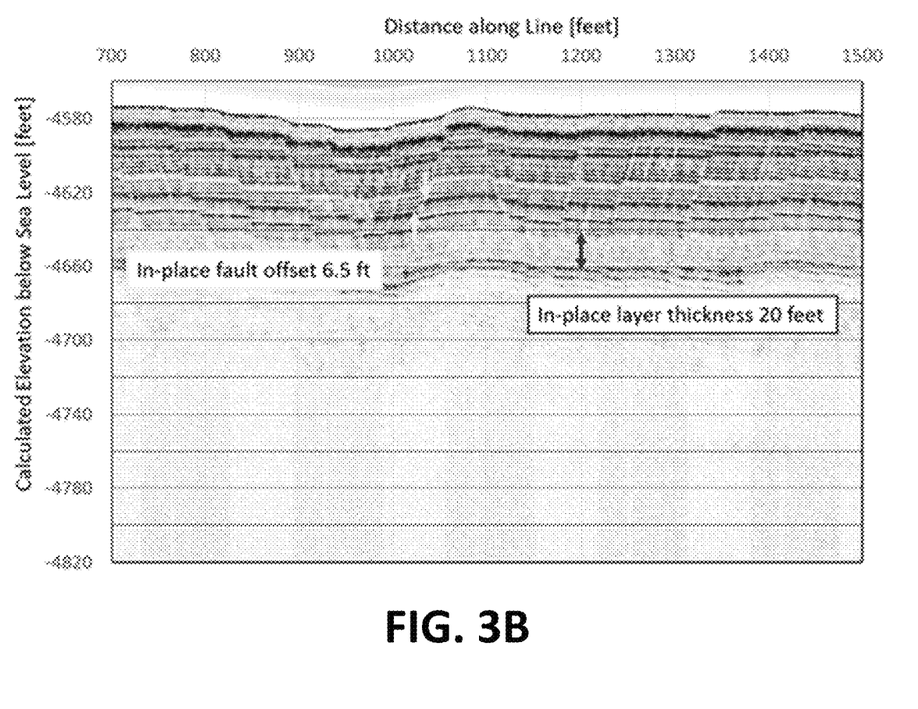
FIG. 3B illustrates an example digital representation of a subsurface region

FIG. 3B illustrates an example digital representation of the subsurface region shown in FIG. 3A, with the travel time of acoustic waves converted into spatial depth. The travel time of acoustic waves in FIG. 3A may be used to calculate elevation/location of the layers and/or other subsurface feature below sea level. The digital representation may provide a visual representation of current/measured thicknesses/depths of layers and/or other subsurface features within the subsurface region. The digital representation may not account for compaction that have occurred within the subsurface region.

Estimates of the magnitude of past events in the subsurface region (e.g., from sub-seafloor geophysical data) may be greatly underestimated as a result of the natural compaction of sediments under the increasing weight of overlying layers. The underestimation may increase as the compaction of layers increases with more sediment deposition. For example, not accounting for compaction of layers within the subsurface region may result in underestimation of the magnitudes of historic sedimentation rates, fault offsets, and mass gravity flow effects. Such underestimation may have a profound effect on quantification of geohazard risk, such as in Probabilistic Fault Displacement Hazard Assessment (methodology to use with deterministic fault displacement estimates to characterize expected fault displacement for design and analysis of new and existing structures and infrastructure). For example, FIG. 3B illustrates example visualization of past events in the subsurface region without accounting for compaction. The digital representation in FIG. 3B may indicate an in-place fault offset of 6.5 feet and an in-place layer thickness of 20 feet. Such analysis of the past events may be incorrect. Analysis of the past events using the digital representation in FIG. 3B may result in underestimation of the past events because the digital representation does not account for compaction that has occurred within the subsurface region.

To address these deficiencies, the present disclosure utilizes amount of void space within layers before compaction to determine decompaction velocity for the layers within the subsurface region. The decompaction velocity may be used as surrogate velocity to determine decompacted thickness/depth of layers and/or other features within the subsurface region without compaction. The decompaction velocity may be used to determine the thickness/depths of layers and/or other features as if no compaction had occurred.

The void information component 104 may be configured to obtain void information for the subsurface region and/or other information. Obtaining void information may include one or more of accessing, acquiring, analyzing, creating, determining, examining, generating, identifying, loading, locating, opening, receiving, retrieving, reviewing, selecting, storing, utilizing, and/or otherwise obtaining the void information. The void information component 104 may obtain void information from one or more locations. For example, the void information component 104 may obtain void information from a storage location, such as the electronic storage 13, electronic storage of a device accessible via a network, and/or other locations. The void information component 104 may obtain void information from one or more hardware components (e.g., a computing device, a component of a computing device) and/or one or more software components (e.g., software running on a computing device). Void information may be stored within a single file or multiple files.

The void information may include information about void amount within the subsurface region. Void amount may refer to amount of void (void space) within the subsurface region. The amount of void within the subsurface region may refer to void ratio within the subsurface region (e.g., ratio of empty space to solid; ratio of fluid to solid). The void information may include information about void amount within different layers within the subsurface region. The void information may include information about void amount at different depths within the subsurface region.

The void information may characterize void amount of the layers within the subsurface region. Void amount of a layer may refer to amount of void (void space) within the layer. The void information may characterize the void amount of the layers within the subsurface region by including information that defines, describes, delineates, identifies, is associated with, quantifies, reflects, sets forth, and/or otherwise characterizes one or more of content, quality, attribute, feature, and/or other aspects of the void amount of the layers within the subsurface region. For example, the void information may characterize the void amount of the layers by including information that specifies the void amount of the layers and/or information that is used to determine the void amount of the layers. Other types of void information are contemplated.

In some implementations, the void amount may include a ratio of fluid to solids within a subsurface volume. A subsurface volume may refer to a volume of earth beneath the subsurface. A surface volume may refer to a volume extracted from a subsurface region. The void space within the subsurface region may be filed with fluid. For example, void space within a subsurface region under water (e.g., under the sea), the void spaces may be filled with water. As compaction occurs, void space may be reduced in size and fluid may be squeezed out of the void space.

The void amount within the subsurface region may be determined by measuring how much fluid is contained within subsurface volumes extracted from the subsurface region. For example, the ratio of fluid to solids within the subsurface volume may be determined based on measurement of moisture content within the subsurface volume and/or other information. By measuring moisture content of subsurface volume extracted from different locations/depths within the subsurface region, the void amount at different locations/depths within the subsurface region may be determined.

Figure 4:
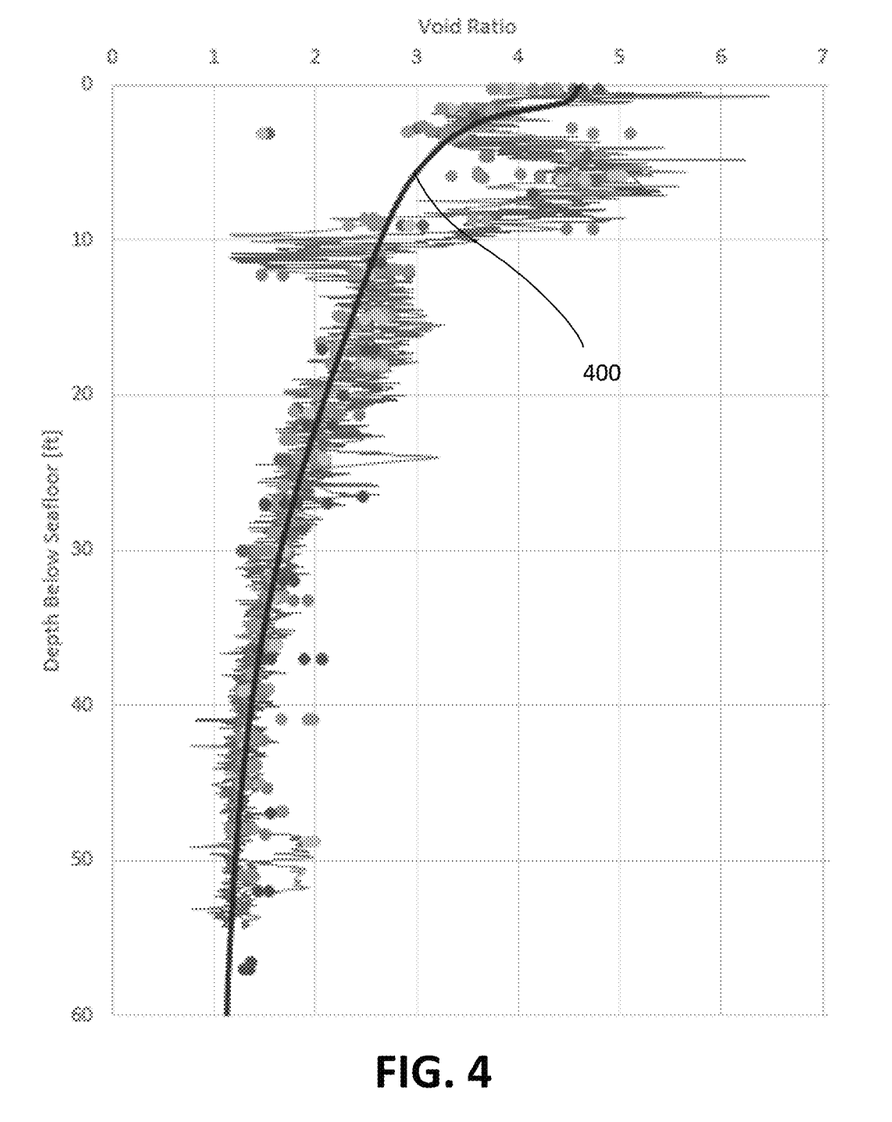
FIG. 4 illustrates an example relationship between void ratio and depth below the seafloor.

FIG. 4 illustrates an example relationship between void ratio and depth below the seafloor. A line 400 shows a smooth change of void ratio as a function of depth. The line 400 may be determined based on the data points of void ratios to depths. In determining the line 400, data points may be weighed equally or differently. In determining the line 400, one or more data points may be excluded. For example, data points from unusually high plasticity clays between about 5- and 10-ft penetration may be disregarded in determining the line 400 because they are not representative of the deeper sediments.

As shown in FIG. 4, void ratio (ratio of fluid to solids) in the subsurface region may change with depth. Void ratio may decrease with increasing depth, indicating that greater amount of compaction has occurred at greater depths within the subsurface region. For instance, void ratio may approach a value of one with increasing depth. That is, at depths greater than 60 ft, the ratio of fluid to solids may approach 1:1. At/near the seafloor, the void ratio may be a value of 4.5. That is, at depths near 0ft, the ratio of fluid to solids may be 4.5:1. The amount of void/void ratio at different depths may be used to determine how much compaction has occurred at different depths.

The decompacted void amount component 106 may be configured to determine decompacted void amount of the layers within the subsurface region. Determining decompacted void amount of the layers within the subsurface region may include ascertaining, choosing, establishing, finding, identifying, obtaining, selecting, setting, and/or otherwise determining the decompacted void amount of the layers within the subsurface region. The decompacted void amount may represent amount of void (void space) within the layers before/without compaction of the layers (e.g., at/near deposition). The decompacted void amount may refer to decompacted void ratio within the subsurface region. The decompacted void amount may correspond to ratio of empty space/fluid to solids within the layers before compaction of the layers.

In some implementations, the decompacted void amount of the layers within the subsurface region may be determined based on user input. For instance, user input may specify the decompacted void amount and/or parameters to be used in calculating the decompacted void amount. In some implementations, the decompacted void amount of the layers within the subsurface region may be determined based on information relating to materials within the layers, deposition condition, and/or other information. For example, different materials within the layers may be deposited with different void ratio. Different deposition condition may result in different void ratio within the layers at deposition.

The decompacted void amount may be determined by increasing from the amount of void (void space) as characterized by the void information. The decompacted void amount may be determined by increasing from the current/measured amount of void (void space) within the subsurface region. For example, the ratio of fluid to solids within the subsurface volume may be increased in the decompacted void amount of the layers within the subsurface region. That is, the void ratio before compaction may be larger than the void ratio after compaction. The amount by which the void ratio is increased may get larger with deeper depths to account for greater compaction at deeper depths.

The decompaction velocity component 108 may be configured to determine decompaction velocity for the layers within the subsurface region. Determining decompaction velocity for the layers within the subsurface region may include ascertaining, choosing, establishing, finding, identifying, obtaining, selecting, setting, and/or otherwise determining the decompaction velocity for the layers within the subsurface region. The decompaction velocity may refer to surrogate velocity to be used in place of actual/measured velocity of acoustic wave in the subsurface region in determining thickness of the layers within the subsurface region. The decompaction velocity may refer to surrogate velocity that is used to artificially expand thickness of layers within the subsurface region to thickness they would have been had compaction not occurred. The decompaction velocity may be used as a surrogate velocity in determining the thickness/depth of layers and/or other features within the subsurface region without/before compaction.

The decompaction velocity for the layers within the subsurface region may be determined based on the decompacted void amount of the layers within the subsurface region, and/or other information. The decompaction velocity for the layers within the subsurface region may be determined based on the decompacted void ratio within the subsurface region. Different values of decompaction velocity may be determined for layers having different decompacted void amount/decompacted void ratio. Different values of decompaction velocity may be determined for different locations within the subsurface region. The values of the decompaction velocity at different locations may be merged into a decompaction velocity profile. The decompaction velocity may be determined to be faster than the current/measured velocity of acoustic wave within the subsurface region. The decompaction velocity may increase with deeper depths to account for greater compaction at deeper depths.

In some implementations, the decompaction velocity for the layers within the subsurface region may be determined based on the decompacted void amount of the layers within the subsurface region by (1) determining expanded thickness of the layers within the surface region based on the decompacted void amount of the layers, and (2) determining the decompaction velocity for the layers based on the expanded thickness of the layers and the travel times of acoustic waves that reflected off the layers within the subsurface region.

Determining expanded thickness of the layers within the subsurface region may include estimation of layer thicknesses if the layers had not been compacted. The expanded thickness of the layers may be determined by increasing the thickness of the layers in accordance with increased amount of void within the decompacted void amount compared to the measured/current void amount within the layers. Increase in the amount of void (void ratio) in a layer may cause the amount of space taken by the layer to be increased. That is, addition of void spaces in the layer may cause the thickness of the layer to increase. Increasing thickness of a layer may cause the depth of the layer to move further beneath the surface.

The expanded thickness of the layers may be divided by the travel times of the acoustic waves within the layers to determine the decompaction velocity for the layers. For example, the expanded thickness of a particular layer may be determined based on decompacted void amount within the layer. This expanded thickness may be divided by the travel time of acoustic wave through the layer to calculate the decompaction velocity for the layer.

Figure 5:
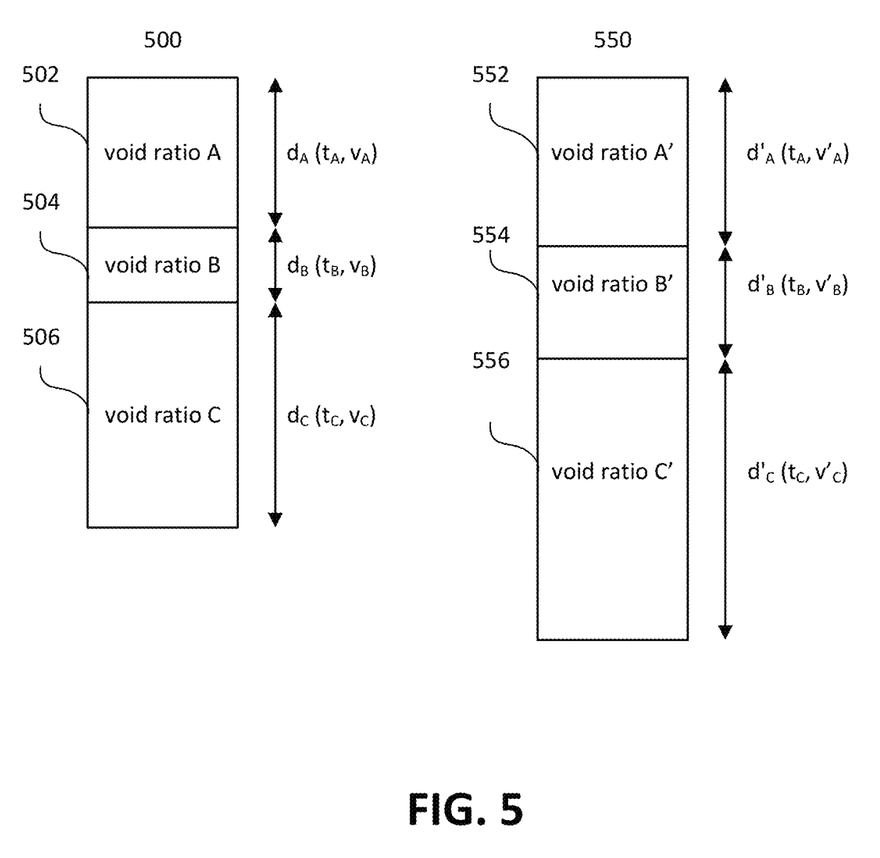
FIG. 5 illustrate example thickness expansion of layers.

FIG. 5 illustrate example thickness expansion of layers. FIG. 5 may include a column 500 representing a column of earth under the surface (e.g., undersea column). The column 500 may include layers 502, 504, 506. The layer 502 may have a void ratio A, the layer 504 may have a void ratio B, and the layer 506 may have a void ratio C. The travel time of acoustic wave (duration of time it takes for acoustic wave to travel through the layer) through the layer 502 may be $t_A$, and the velocity of acoustic wave through the layer 502 may be $v_A$. Current/measured thickness of the layer 502, $d_A$, may be calculated by multiplying the velocity $v_A$ by the travel time $t_A$. The travel time of acoustic wave through the layer 504 may be $t_B$, and the velocity of acoustic wave through the layer 504 may be $v_B$. Current/measured thickness of the layer 504, dB, may be calculated by multiplying the velocity $v_B$ by the travel time $t_B$. The travel time of acoustic wave through the layer 506 may be $t_c$, and the velocity of acoustic wave through the layer 504 may be $v_c$. Current/measured thickness of the layer 506, dc, may be calculated by multiplying the velocity $v_c$ by the travel time $t_c$.

A decompacted column 550 may represent the column of earth with compaction removed. The decompacted column 550 may include decompacted layers 552, 554, 556. The decompacted layer 552 may be a decompacted version of the layer 502, the decompacted layer 554 may be a decompacted version of the layer 504, and the decompacted layer 556 may be a decompacted version of the layer 506. The decompacted layers 552, 554, 556 may be thicker/penetrate deeper into the earth than the corresponding layers 502, 504, 506. The expanded thickness of the decompacted layers 552, 554, 556 may be estimated by determining decompacted void ratios. For example, the decompacted void ratio for the decompacted layer 552 may be determined to be void ratio A', which may be larger than void ratio A of the layer 502. The decompacted void ratio for the decompacted layer 554 may be determined to be void ratio B', which may be larger than void ratio B of the layer 504. The decompacted void ratio for the decompacted layer 556 may be determined to be void ratio C', which may be larger than void ratio C of the layer 506.

Based on the corresponding decompacted void ratio, the expanded thickness of the decompacted layer 552 may be determined to be d'A, which may be thicker than thickness $d_A$ of the layer 502. The expanded thickness of the decompacted layer 554 may be determined to be d'B, which may be thicker than thickness dB of the layer 504. The expanded thickness of the decompacted layer 556 may be determined to be d'c, which may be thicker than thickness dc of the layer 506. The decompaction velocity $V'_A$ corresponding to the decompacted layer 552 may be calculated by dividing the expanded thickness d'A by the travel time $t_A$. The decompaction velocity $V'_A$ corresponding to the decompacted layer 554 may be calculated by dividing the expanded thickness d'B by the travel time $t_B$. The decompaction velocity v'c corresponding to the decompacted layer 556 may be calculated by dividing the expanded thickness $d'_c$ by the travel time $t_c$.

The decompacted thickness component 110 may be configured to determine decompacted thickness of the layers within the subsurface region. Determining decompacted thickness of the layers within the subsurface region may include ascertaining, choosing, establishing, finding, identifying, obtaining, selecting, setting, and/or otherwise determining the decompacted thickness of the layers within the subsurface region. Determining decompacted thickness of the layers within the subsurface region may include determining depths of the layers within the subsurface region. The decompacted thickness of the layers may refer to thickness the layers would have had if compaction of soil did not occur within the layers. The decompacted thickness of the layers may refer to thickness of the layers if compaction of the layers were reversed.

The decompacted thickness of the layers within the subsurface region may be determined based on the decompaction velocity for the layers within the subsurface region, the travel times of the acoustic waves that reflected off the layers within the subsurface region, and/or other information. The decompaction velocity for the layers (e.g., different values of decompaction velocity, decompaction velocity profile) may be multiplied by the travel times of the acoustic waves through the layers to calculate the decompacted thickness of the layers. For example, the decompaction velocity for a particular layer may be multiplied by the amount of time it takes for acoustic waves to travel through the layer to calculate the decompacted thickness of the layer.

In some implementations, determining the decompacted thickness of the layers within the subsurface region based on the decompaction velocity for the layers within the subsurface region and the travel times of the acoustic waves that reflected off the layers within the subsurface region may include generating one or more decompacted digital representations of the subsurface region. A decompacted digital representation may provide visual representation of the layers and/or other subsurface features within the subsurface region in which compaction of the layers have been reversed. A decompacted digital representation may provide visual representation of the layers and/or other subsurface features within the subsurface region had no compaction occurred within the subsurface region.

A decompacted digital representation of the subsurface region may be generated by applying the decompaction velocity for the layers within the subsurface region to the travel times of the acoustic waves that reflected off the layers within the subsurface region. For example, different values of decompaction velocity for different layers may be multiplied with the corresponding travel times of the acoustic waves to generate the decompacted digital representation of the subsurface region. That is, a decompacted profile of the subsurface region may be generated by applying the decompaction velocity to the travel times of the acoustic waves. Such post-processing of the travel times (e.g., reflection seismic data) may allow for indirect measurement of decompacted thickness of the layers and the decompacted depths between acoustic reflectors within the subsurface region. Such post-processing of the travel times (e.g., reflection seismic data) may allow for indirect measurement of decompacted positions of subsurface features within the subsurface region.

In some implementations, analysis of past events within the subsurface region may be performed based on the decompacted digital representation(s) of the subsurface region and/or other information. Past events within the subsurface region may refer to geologic events that have occurred in the past within the subsurface region. Past events within the subsurface region may refer to events in the past that have affected/changed the configuration of subsurface materials within the subsurface region. For example, the past events within the subsurface region may include fault activity (e.g., fault displacement) within the subsurface region. As another example, the past events within the subsurface region may include erosion and/or deposition within the subsurface region (e.g., mass gravity flow effects). Analysis of other types of past events is contemplated.

In some implementations, usage of the decompacted digital representation of the subsurface region for the analysis of the past events within the subsurface region may reduce underestimation of the past events within the subsurface region. The decompacted digital representation may provide for more accurate analysis of the past events than digital representation that have not taken compaction of layers into account. For instance, analysis of the past events using a non-decompacted digital representation may lead to a faulty conclusion that the subsurface region has experienced increasing fault activity over a geologic time, while using a decompacted digital representation may lead to the correct conclusion that the subsurface region has experienced decreasing fault activity over the geologic time. Use of the decompacted digital representation may result in more accurate evaluation of the magnitude of erosion and deposition within the subsurface region (e.g., during past submarine landslide events).

Figure 6:
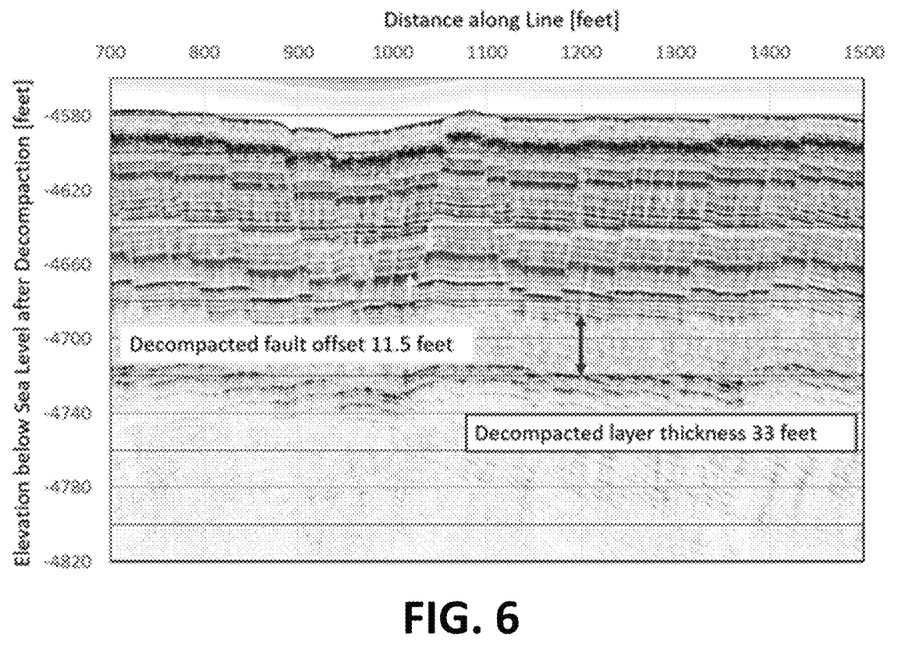
FIG. 6 illustrates an example decompacted digital representation of a subsurface region.

FIG. 6 illustrates an example decompacted digital representation of the subsurface region shown in FIGS. 3A and 3B. The decompacted digital representation may be generated by applying the decompaction velocity for the layers within the subsurface region to the travel times of the acoustic waves through the layers within the subsurface region. The layers in the decompacted digital representation in FIG. 6 may be thicker than the layers in the digital representation in FIG. 3B. For example, a layer having a thickness of 20 feet in FIG. 3B may have a thickness of 33 feet in FIG. 6. The decompaction of layers may enable more accurate analysis of past events within the subsurface region. For instance, the digital representation in FIG. 3B may show an in-place fault offset of 6.5 feet, but the decompacted digital representation in FIG. 6 may show a more accurate fault offset of 11.5 feet.

In some implementations, decompaction of layer thickness and/or analysis of past events within the subsurface region may be performed based on one or more correlations/relationships between depths and travel time of acoustic wave. For example, correlations/relationships may be established between (1) void ratio and depth, and (2) acoustic wave velocity and void ratio. The two correlations/relationships may be used to establish a correlation/relationship between depth and velocity/travel time (e.g., two-way travel time). A correlation/relationship may be established between depth and travel time to account for compaction of layers within the subsurface region. Such correlation/relationship may be used as a scaling function to estimate past events (e.g., fault offsets) at the time of their occurrence.

While implementations of the disclosure have been described with respect to subsurface regions beneath the sea, this is merely as an example and is not meant to be limiting. Present disclosure may be applied to other subsurface regions.

Implementations of the disclosure may be made in hardware, firmware, software, or any suitable combination thereof. Aspects of the disclosure may be implemented as instructions stored on a machine-readable medium, which may be read and executed by one or more processors. A machine-readable medium may include any mechanism for storing or transmitting information in a form readable by a machine (e.g., a computing device). For example, a tangible computer-readable storage medium may include read-only memory, random access memory, magnetic disk storage media, optical storage media, flash memory devices, and others, and a machine-readable transmission media may include forms of propagated signals, such as carrier waves, infrared signals, digital signals, and others. Firmware, software, routines, or instructions may be described herein in terms of specific exemplary aspects and implementations of the disclosure, and performing certain actions.

In some implementations, some or all of the functionalities attributed herein to the system 10 may be provided by external resources not included in the system 10. External resources may include hosts/sources of information, computing, and/or processing and/or other providers of information, computing, and/or processing outside of the system 10.

Although the processor 11 and the electronic storage 13 are shown to be connected to the interface 12 in FIG. 1, any communication medium may be used to facilitate interaction between any components of the system 10. One or more components of the system 10 may communicate with each other through hard-wired communication, wireless communication, or both. For example, one or more components of the system 10 may communicate with each other through a network. For example, the processor 11 may wirelessly communicate with the electronic storage 13. By way of non-limiting example, wireless communication may include one or more of radio communication, Bluetooth communication, Wi-Fi communication, cellular communication, infrared communication, or other wireless communication. Other types of communications are contemplated by the present disclosure.

Although the processor 11 is shown in FIG. 1 as a single entity, this is for illustrative purposes only. In some implementations, the processor 11 may comprise a plurality of processing units. These processing units may be physically located within the same device, or the processor 11 may represent processing functionality of a plurality of devices operating in coordination. The processor 11 may be separate from and/or be part of one or more components of the system 10. The processor 11 may be configured to execute one or more components by software; hardware; firmware; some combination of software, hardware, and/or firmware; and/or other mechanisms for configuring processing capabilities on the processor 11.

It should be appreciated that although computer program components are illustrated in FIG. 1 as being co-located within a single processing unit, one or more of computer program components may be located remotely from the other computer program components. While computer program components are described as performing or being configured to perform operations, computer program components may comprise instructions which may program processor 11 and/or system 10 to perform the operation.

While computer program components are described herein as being implemented via processor 11 through machine-readable instructions 100, this is merely for ease of reference and is not meant to be limiting. In some implementations, one or more functions of computer program components described herein may be implemented via hardware (e.g., dedicated chip, field-programmable gate array) rather than software. One or more functions of computer program components described herein may be software-implemented, hardware-implemented, or software and hardware-implemented The description of the functionality provided by the different computer program components described herein is for illustrative purposes, and is not intended to be limiting, as any of computer program components may provide more or less functionality than is described. For example, one or more of computer program components may be eliminated, and some or all of its functionality may be provided by other computer program components. As another example, processor 11 may be configured to execute one or more additional computer program components that may perform some or all of the functionality attributed to one or more of computer program components described herein.

The electronic storage media of the electronic storage 13 may be provided integrally (i.e., substantially non-removable) with one or more components of the system 10 and/or as removable storage that is connectable to one or more components of the system 10 via, for example, a port (e.g., a USB port, a Firewire port, etc.) or a drive (e.g., a disk drive, etc.). The electronic storage 13 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. The electronic storage 13 may be a separate component within the system 10, or the electronic storage 13 may be provided integrally with one or more other components of the system 10 (e.g., the processor 11). Although the electronic storage 13 is shown in FIG. 1 as a single entity, this is for illustrative purposes only. In some implementations, the electronic storage 13 may comprise a plurality of storage units. These storage units may be physically located within the same device, or the electronic storage 13 may represent storage functionality of a plurality of devices operating in coordination.

Figure 2:
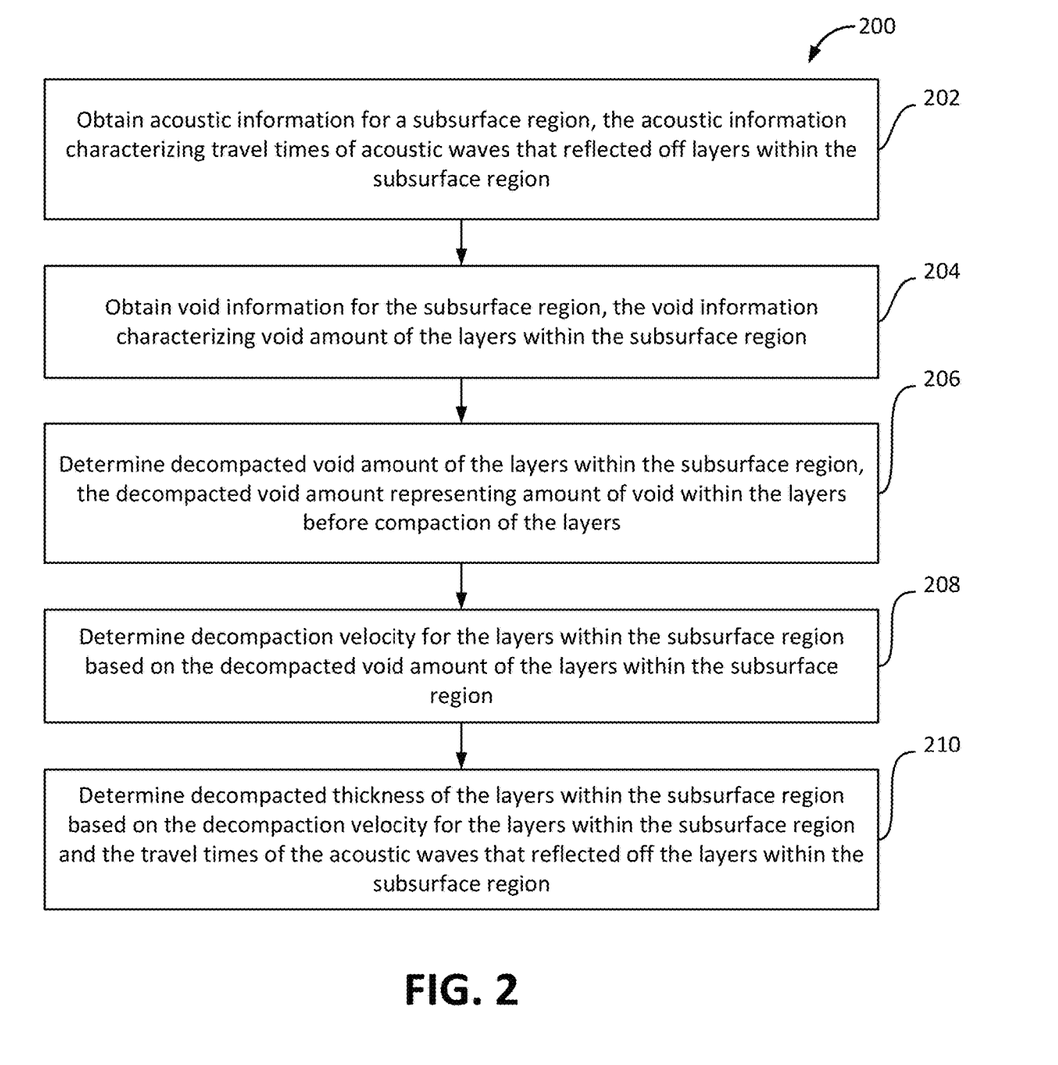
FIG. 2 illustrates an example method for decompacting subsurface data representation.

FIG. 2 illustrates method 200 for decompacting subsurface data. The operations of method 200 presented below are intended to be illustrative. In some implementations, method 200 may be accomplished with one or more additional operations not described, and/or without one or more of the operations discussed. In some implementations, two or more of the operations may occur simultaneously.

In some implementations, method 200 may be implemented in one or more processing devices (e.g., a digital processor, an analog processor, a digital circuit designed to process information, a central processing unit, a graphics processing unit, a microcontroller, an analog circuit designed to process information, a state machine, and/or other mechanisms for electronically processing information). The one or more processing devices may include one or more devices executing some or all of the operations of method 200 in response to instructions stored electronically on one or more electronic storage media. The one or more processing devices may include one or more devices configured through hardware, firmware, and/or software to be specifically designed for execution of one or more of the operations of method 200.

Referring to FIG. 2 and method 200, at operation 202, acoustic information for a subsurface region may be obtained. The acoustic information for the subsurface region may characterize travel times of acoustic waves that reflected off layers within the subsurface region. In some implementation, operation 202 may be performed by a processor component the same as or similar to the acoustic information component 102 (Shown in FIG. 1 and described herein).

At operation 204, void information for the subsurface region may be obtained. The void information for the subsurface region may characterize void amount of the layers within the subsurface region. In some implementation, operation 204 may be performed by a processor component the same as or similar to the void information component 104 (Shown in FIG. 1 and described herein).

At operation 206, decompacted void amount of the layers within the subsurface region may be determined. The decompacted void amount may represent amount of void within the layers before compaction of the layers. In some implementation, operation 206 may be performed by a processor component the same as or similar to the decompacted void amount component 106 (Shown in FIG. 1 and described herein).

At operation 208, decompaction velocity for the layers within the subsurface region may be determined based on the decompacted void amount of the layers within the subsurface region, and/or other information. In some implementation, operation 208 may be performed by a processor component the same as or similar to the decompaction velocity component 108 (Shown in FIG. 1 and described herein).

At operation 210, decompacted thickness of the layers within the subsurface region may be determined based on the decompaction velocity for the layers within the subsurface region, the travel times of the acoustic waves that reflected off the layers within the subsurface region, and/or other information. In some implementation, operation 210 may be performed by a processor component the same as or similar to the decompacted thickness component 110 (Shown in FIG. 1 and described herein).

Although the system(s) and/or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A system for decompacting subsurface data, the system comprising:
    an acoustic wave generator/transmitter for sending acoustic waves into a subsurface region, the acoustic waves penetrating into the subsurface region, reflecting off layers within the surface region, and returning for detection;
    an acoustic wave detector/receiver for receiving the acoustic waves and measuring travel times of the acoustic waves that reflected off the layers within the subsurface region;
    one or more physical processors configured by machine-readable instructions to:
        determine void amount of the layers within the subsurface by measuring moisture content within samples extracted from the subsurface region;
        determine decompacted void amount of the layers within the subsurface region, the decompacted void amount representing amount of void within the layers without compaction of the layers, wherein the decompacted void amount of the layers is determined based on materials within the layers and/or deposition conditions for the layers;
        determine surrogate decompaction velocity for the layers within the subsurface region based on the decompacted void amount of the layers within the subsurface region, the surrogate decompaction velocity including a surrogate velocity used in place of actual or measured velocity of the acoustic waves to artificially expand thickness of the layers within the subsurface region to thickness without compaction, wherein determining the decompaction velocity for the layers within the subsurface region based on the decompacted void amount of the layers within the subsurface region includes:
            determining expanded thickness of the layers based on the decompacted void amount of the layers, the expanded thickness of the layer including estimation of the thickness of the layers without compaction via increasing the thickness of the layers in accordance with increase in the amount of void from the measured void amount to the decompacted void amount; and
            determining the surrogate decompaction velocity for the layers based on the expanded thickness of the layers and the measured travel times of acoustic waves that reflected off the layers within the subsurface region;
        generate a decompacted digital representation of the subsurface region by applying the surrogate decompaction velocity for the layers within the subsurface region to the measured travel times of the acoustic waves that reflected off the layers within the subsurface region, the decompacted digital representation of the subsurface region including artificially expanded thickness of the layers of the subsurface region in image form by applying the surrogate decompaction velocity to the measured travels times of the acoustic waves, wherein the decompacted digital representation of the subsurface region enables indirect measurement of decompacted thickness of the layers within the subsurface region, decompacted depths between acoustic reflectors within the subsurface region, and decompacted positions of subsurface features within the subsurface region; and
        perform analysis of past events within the subsurface region based on the decompacted digital representation of the subsurface region, wherein usage of the decompacted digital representation of the subsurface region for the analysis of the past events within the subsurface region provides more accurate analysis of the past events within the subsurface region than usage of a non-decompacted digital representation of the subsurface region.

2. The system of claim 1, wherein the void amount includes a ratio of fluid to solids within a subsurface volume.

3. The system of claim 2, wherein the ratio of fluid to solids within the subsurface volume is increased in the decompacted void amount of the layers within the subsurface region.

4. The system of claim 1, wherein the past events within the subsurface region include fault activity within the subsurface region.

5. The system of claim 1, wherein the past events within the subsurface region include erosion and deposition within the subsurface region.

6. The system of claim 1, wherein the usage of the decompacted digital representation of the subsurface region for the analysis of the past events within the subsurface region reduces underestimation of the past events within the subsurface region.

7. A method for decompacting subsurface data, the method comprising:
    sending, by an acoustic wave generator/transmitter, acoustic waves into a subsurface region, the acoustic wave penetrating into the subsurface region, reflecting off layers within the surface region, and returning for detection;
    receiving, by an acoustic wave detector/receiver, the acoustic waves and measuring travel times of the acoustic waves that reflected off the layers within the subsurface region;
    determining void amount of the layers within the subsurface by measuring moisture content within samples extracted from the subsurface region;
    determining decompacted void amount of the layers within the subsurface region, the decompacted void amount representing amount of void within the layers without compaction of the layers, wherein the decompacted void amount of the layers is determined based on materials within the layers and/or deposition conditions for the layers;

determining surrogate decompaction velocity for the layers within the subsurface region based on the decompacted void amount of the layers within the subsurface region, the surrogate decompaction velocity including a surrogate velocity used in place of actual or measured velocity of the acoustic waves to artificially expand thickness of the layers within the subsurface region to thickness without compaction, wherein determination of the decompaction velocity for the layers within the subsurface region based on the decompacted void amount of the layers within the subsurface region includes:

determination of expanded thickness of the layers based on the decompacted void amount of the layers, the expanded thickness of the layer including estimation of the thickness of the layers without compaction via increasing the thickness of the layers in accordance with increase in the amount of void from the measured void amount to the decompacted void amount; and determination of the surrogate decompaction velocity for the layers based on the expanded thickness of the layers and the measured travel times of acoustic waves that reflected off the layers within the subsurface region;

generating a decompacted digital representation of the subsurface region by applying the surrogate decompaction velocity for the layers within the subsurface region to the measured travel times of the acoustic waves that reflected off the layers within the subsurface region, the decompacted digital representation of the subsurface region including artificially expanded thickness of the layers of the subsurface region in image form by applying the surrogate decompaction velocity to the measured travels times of the acoustic waves, wherein the decompacted digital representation of the subsurface region enables indirect measurement of decompacted thickness of the layers within the subsurface region, decompacted depths between acoustic reflectors within the subsurface region, and decompacted positions of subsurface features within the subsurface region; and performing analysis of past events within the subsurface region based on the decompacted digital representation of the subsurface region, wherein usage of the decompacted digital representation of the subsurface region for the analysis of the past events within the subsurface region provides more accurate analysis of the past events within the subsurface region than usage of a non-decompacted digital representation of the subsurface region.

8. The method of claim 7, wherein the void amount includes a ratio of fluid to solids within a subsurface volume.

9. The method of claim 8, wherein the ratio of fluid to solids within the subsurface volume is increased in the decompacted void amount of the layers within the subsurface region.

10. The method of claim 7, wherein the past events within the subsurface region include fault activity within the subsurface region.

11. The method of claim 7, wherein the past events within the subsurface region include erosion and deposition within the subsurface region.

12. The method of claim 7, wherein the usage of the decompacted digital representation of the subsurface region for the analysis of the past events within the subsurface region reduces underestimation of the past events within the subsurface region.

13. The system of claim 4, wherein the usage of the decompacted digital representation of the subsurface region for the analysis of the past events within the subsurface region providing more accurate analysis of the past events within the subsurface region than the usage of the non-decompacted digital representation of the subsurface region includes:

the usage of the non-decompacted digital representation of the subsurface region leading to a faulty conclusion that the subsurface region has experienced increasing fault activity over a geologic time; and the usage of the decompacted digital representation of the subsurface region leading to a correct conclusion that the subsurface region has experienced decreasing fault activity over the geologic time.

14. The system of claim 5, wherein the usage of the decompacted digital representation of the subsurface region for the analysis of the past events within the subsurface region providing more accurate analysis of the past events within the subsurface region than the usage of the non-decompacted digital representation of the subsurface region includes the usage of the decompacted digital representation of the subsurface region leading to more accurate evaluation of magnitude of the erosion and the deposition within the subsurface region.

15. The method of claim 10, wherein the usage of the decompacted digital representation of the subsurface region for the analysis of the past events within the subsurface region providing more accurate analysis of the past events within the subsurface region than the usage of the non-decompacted digital representation of the subsurface region includes:

the usage of the non-decompacted digital representation of the subsurface region leading to a faulty conclusion that the subsurface region has experienced increasing fault activity over a geologic time; and the usage of the decompacted digital representation of the subsurface region leading to a correct conclusion that the subsurface region has experienced decreasing fault activity over the geologic time.

16. The method of claim 11, wherein the usage of the decompacted digital representation of the subsurface region for the analysis of the past events within the subsurface region providing more accurate analysis of the past events within the subsurface region than the usage of the non-decompacted digital representation of the subsurface region includes the usage of the decompacted digital representation of the subsurface region leading to more accurate evaluation of magnitude of the erosion and the deposition within the subsurface region.

* * * * *

UNITED STATES PATENT AND TRADEMARK OFFICE
CERTIFICATE OF CORRECTION

PATENT NO. : 11,892,580 B2
APPLICATION NO. : 17/148111
DATED : February 6, 2024
INVENTOR(S) : Robert Lewis Little It is certified that error appears in the above-identified patent and that said Letters Patent is hereby corrected as shown below:

In the Claims

In Claim 7, Column 16, Line 56, please replace "wave" with --waves--, therefor.

Signed and Sealed this
Twelfth Day of March, 2024

Katherine Kelly Vidal
*Director of the United States Patent and Trademark Office*